US008951500B2

United States Patent
Brindle et al.

(10) Patent No.: US 8,951,500 B2
(45) Date of Patent: Feb. 10, 2015

(54) 13C-MR IMAGING OR SPECTROSCOPY OF CELL DEATH (75) Inventors: Kevin M. Brindle, Cambridge (GB); Samuel Evan Day, Tucson, AR (US); Mikko Iivari Kettunen, Cambridge (GB)

(73) Assignee: GE Healthcare AS, Oslo (NO)

( * ) Notice: Subject to any disclaimer, the term of this patent is extended or adjusted under 35 U.S.C. 154(b) by 1219 days.

(21) Appl. No.: 12/376,470

(22) PCT Filed: Aug. 17, 2007

(86) PCT No.: PCT/NO2007/000286
§ 371 (c)(1),
(2), (4) Date: Feb. 5, 2009

(87) PCT Pub. No.: WO2008/020764
PCT Pub. Date: Feb. 21, 2008

(65) Prior Publication Data
US 2010/0226859 A1  Sep. 9, 2010

(30) Foreign Application Priority Data

Aug. 18, 2006  (NO) .................................. 20063702

(51) Int. Cl.
G01R 33/46  (2006.01)
G01R 33/483  (2006.01)
G01R 33/465  (2006.01)
A61B 5/055  (2006.01)
G01R 33/56  (2006.01)
G01R 33/48  (2006.01)

(52) U.S. Cl.
CPC .............. *G01R 33/465* (2013.01); *A61B 5/055* (2013.01); *G01R 33/483* (2013.01); *G01R 33/5601* (2013.01); *G01R 33/4828* (2013.01)
USPC ............................................ 424/9.3; 435/29

(58) Field of Classification Search
None
See application file for complete search history.

(56) References Cited

U.S. PATENT DOCUMENTS

2004/0092549 A1 *  5/2004  Jariwalla ....................... 514/310

FOREIGN PATENT DOCUMENTS

WO     2006/011810       2/2006
WO     2006054903 A2     5/2006
WO     WO 2006054903 A2 *  5/2006

OTHER PUBLICATIONS

EO Abogaye, ZM Bhujwalla, DC Shungu, JD Glickson. "Detection of Tumor Response to Chemotherapy by 1H Nuclear Magnetic Resonance Spectroscopy: Effect of 5-Fluorouracil on Lactate Levels in Radiation-induced Fibrosarcoma 1 Tumors." Cancer Research, vol. 58, Mar. 1, 1998, pp. 1063-1067.*
Golman, K. et.al. "Real-time metabolic imaging" Proceedings of the National Academy of Science in the Untied States of America, vol. 103, No. 30, Jul. 25, 2006, pp. 11270-11275.
Kettunen, et.al. "Apoptosis detection using magnetic resonance imaging and spectroscopy" Progress in NMR Spectroscopy, Pergamon Press, GB, vol. 47, No. 3-4, Dec. 15, 2005, pp. 175-185.
Day, S.E., et.al. "detecting tumor response to treatment using hyperpolarized 13C magnetic resonance imaging and spectroscopy" Nature Medicine, vol. 13, No. 11, Oct. 28, 2007, pp. 1382-1387.
PCT/NO2007/000286 Int'l Search Report/Written Opinion dated Dec. 10, 2007.

* cited by examiner

*Primary Examiner* — Frederick Krass
*Assistant Examiner* — Isaac Shomer
(74) *Attorney, Agent, or Firm* — Jean K. Testa (57) ABSTRACT The invention relates to method of $^{13}$C-MR imaging and/or $^{13}$C-MR spectroscopy of cell death using an imaging medium which comprises hyperpolarized $^{13}$C-pyruvate.

9 Claims, 3 Drawing Sheets

Lactate labelling (mM/sec)

13C-MR IMAGING OR SPECTROSCOPY OF CELL DEATH

This application is a filing under 35 U.S.C. 371 of international application number PCT/NO2007/000286, filed Aug. 17, 2007, which claims priority to application number 20063702 filed Aug. 18, 2006, in Norway the entire disclosure of which is hereby incorporated by reference.

The invention relates to a method of $^{13}$C-MR imaging or spectroscopy of cell death using an imaging medium which comprises hyperpolarised $^{13}$C-pyruvate.

Cell death may arise through a variety of mechanisms. Several of these mechanisms are well characterized, including apoptosis and necrosis.

Apoptosis, or programmed cell death, plays an important role in the control of development and in the maintenance of tissue homeostatis in multi-cellular organisms. Apoptosis progresses through a series of energy-requiring and tightly-regulated steps that conclude with the engulfment of dying cells by neighbouring phagocytic cells, in a process that avoids the inflammatory reaction caused by cellular necrosis. In mammalian cells, apoptosis is mediated by two major signalling pathways: the first is though an extrinsic pathway initiated via cell surface death receptors and the second is through intrinsic initiators, such as DNA damage. Both of these pathways converge at the surface of the mitochondria.

Apoptosis is a critical event in numerous processes within the mammalian body. For example embryonic development is highly reliant on apoptosis, and tissues that turnover rapidly require tight regulation to avoid serious pathological consequences. Failure to regulate apoptosis, i.e. insufficient or too much cell death, result in pathological conditions like cancer and autoimmune diseases (insufficient), or neurodegenerative diseases like Alzheimer (too much cell death). Hence there is an interest in identifying apoptosis non-invasively in vivo in the human or non-human animal body.

Necrosis is a form of accidental cell death that results from prolonged exposure to injury, infection, cancer, infarction, poisons and inflammation. Severe damage to one essential system in the cell leads to secondary damage to other systems, a so-called cascade of effects. Necrosis is characterised by randomly sized DNA fragments, free radical formation, swelling of the cell and loss of membrane integrity resulting in release of cellular contents.

Necrosis can arise from lack of proper care to a site of injury, infection or infarction. Infarctions occur for instance in the myocardium but also in other tissues, especially in the brain. While infarction can be healed to a certain extent, in the case of necrosis, only the harmful sequels for the rest of the organism can be prevented or at least mitigated. As with infarction, knowing the extent and nature of a necrosis is important for further medical treatment. Hence there is an interest in identifying necrosis non-invasively in vivo in the human or non-human animal body Several imaging modalities to image cell death in the human or non-human animal body are known in the art. Radiopharmaceuticals for cell death imaging have been reviewed by Lahorte et al., Eur. J. Nucl. Med. 31 (2004), 887. PET imaging with 18F-FDG, alone or in combination with CT has also been used for the detection of cell death, see for instance Romer et al., Blood 91 (1998), 4464 or von Schulthess et al, Radiology 238 (2006), 405.

Magnetic resonance (MR) detection like for instance MR imaging (MRI) and MR spectroscopy (MRS) could be valuable tools for detecting cell death and these tools have become particularly attractive to physicians as they allow for obtaining images of a patients body or parts thereof in a non-invasive way and without exposing the patient and the medical personnel to potentially harmful radiation such as X-ray. Because of its high quality images and good spatial and temporal resolution, MRI is the favourable imaging technique of soft tissue and organs.

MR-based methods to detect cell death have been the subject of several recent reviews, for instance Kettunen et al., Prog. Nucl. Mag. Res. Sp. 47 (2005), 175 or Hakumäki et al., Eur. J. Radiol. 56 (2005), 143.

It has now been found that hyperpolarised $^{13}$C-pyruvate can be used as an agent for detecting cell death in the human or non-human animal body using $^{13}$C-MR imaging or $^{13}$C-MR spectroscopy.

Pyruvate is an endogenous compound which is very well tolerated by the human body, even in high concentrations. As a precursor in the citric acid cycle, pyruvate plays an important metabolic role in the human body. Pyruvate is converted into different compounds: its transamination results in alanine, via oxidative decarboxylation, pyruvate is converted into acetyl-CoA and carbon dioxide (which is further converted to bicarbonate), the reduction of pyruvate results in lactate and its carboxylation in oxaloacetate.

Further, the metabolic conversion of hyperpolarised $^{13}$C-pyruvate into its metabolites hyperpolarised $^{13}$C-lactate, hyperpolarised $^{13}$C-bicarbonate (in the case of $^{13}$C$_1$-pyruvate, $^{13}$C$_{1,2}$-pyruvate or $^{13}$C$_{1,2,3}$-pyruvate only) and hyperpolarised $^{13}$C-alanine can be used to study metabolic processes in the human body using MR. $^{13}$C$_1$-pyruvate has a T$_1$ relaxation in human full blood at 37° C. of about 42 s, however, the conversion of hyperpolarised $^{13}$C-pyruvate to hyperpolarised $^{13}$C-lactate, hyperpolarised $^{13}$C-bicarbonate and hyperpolarised $^{13}$C-alanine has been found to be fast enough to allow signal detection from the $^{13}$C-pyruvate parent compound and its metabolites. The amount of alanine, bicarbonate and lactate is dependent on the metabolic status of the tissue under investigation. The MR signal intensity of hyperpolarised $^{13}$C-lactate, hyperpolarised $^{13}$C-bicarbonate and hyperpolarised $^{13}$C-alanine is related to the amount of these compounds and the degree of polarisation left at the time of detection, hence by monitoring the conversion of hyperpolarised $^{13}$C-pyruvate to hyperpolarised $^{13}$C-lactate, hyperpolarised $^{13}$C-bicarbonate and hyperpolarised $^{13}$C-alanine it is possible to study metabolic processes in vivo in the human or non-human animal body by using non-invasive MR imaging or MR spectroscopy.

It has been found that the MR signal amplitudes arising from the different pyruvate metabolites varies depending on the tissue type. The unique metabolic peak pattern formed by alanine, lactate, bicarbonate and pyruvate can be used as fingerprint for the metabolic state of the tissue under examination and thus allows for the discrimination between healthy tissue and tumour tissue. The use of hyperpolarised $^{13}$C-pyruvate for tumour imaging—with tumour tissue showing high metabolic activity—has been described in detail in WO-A-2006/011810.

Further, the use of hyperpolarised $^{13}$C-pyruvate for cardiac imaging has been described in WO-A-2006/054903.

Thus, in a first aspect the invention provides a method of $^{13}$C-MR imaging and/or $^{13}$C-MR spectroscopy for detecting cell death using an imaging medium comprising hyperpolarised $^{13}$C-pyruvate.

The term "cell death" denotes all forms of cell death arising from a variety of mechanisms. The term includes apoptosis and necrosis.

The term "$^{13}$C-pyruvate" denotes a salt of $^{13}$C-pyruvic acid.

The terms "hyperpolarised" and "polarised" are used interchangeably hereinafter and denote a nuclear polarisation level in excess of 0.1%, more preferred in excess of 1% and most preferred in excess of 10%.

The level of polarisation may for instance be determined by solid state $^{13}$C-NMR measurements in solid hyperpolarised $^{13}$C-pyruvate, e.g. solid hyperpolarised $^{13}$C-pyruvate obtained by dynamic nuclear polarisation (DNP) of $^{13}$C-pyruvate. The solid state $^{13}$C-NMR measurement preferably consists of a simple pulse-acquire NMR sequence using a low flip angle. The signal intensity of the hyperpolarised $^{13}$C-pyruvate in the NMR spectrum is compared with signal intensity of $^{13}$C-pyruvate in a NMR spectrum acquired before the polarisation process. The level of polarisation is then calculated from the ratio of the signal intensities of before and after polarisation.

In a similar way, the level of polarisation for dissolved hyperpolarised $^{13}$C-pyruvate may be determined by liquid state NMR measurements. Again the signal intensity of the dissolved hyperpolarised $^{13}$C-pyruvate is compared with the signal intensity of the dissolved $^{13}$C-pyruvate before polarisation. The level of polarisation is then calculated from the ratio of the signal intensities of $^{13}$C-pyruvate before and after polarisation.

The term "imaging medium" denotes a liquid composition comprising hyperpolarised $^{13}$C-pyruvate as the MR active agent. The imaging medium according to the invention may be used as imaging medium in MR imaging or as MR spectroscopy agent in MR spectroscopy.

The imaging medium according to the method of the invention may be used as imaging medium for in vivo MR imaging and/or spectroscopy, i.e. MR imaging and/or spectroscopy carried out on living human or non-human animal beings. Further, the imaging medium according to the method of the invention may be used as imaging medium for in vitro MR imaging and/or spectroscopy, e.g. for detecting cell death in cell cultures or ex vivo tissues. Cell cultures may be derived from cells obtained from samples derived from the human or non human animal body like for instance blood, urine or saliva while ex vivo tissue may be obtained from biopsies or surgical procedures.

The isotopic enrichment of the hyperpolarised $^{13}$C-pyruvate used in the method of the invention is preferably at least 75%, more preferably at least 80% and especially preferably at least 90%, an isotopic enrichment of over 90% being most preferred. Ideally, the enrichment is 100%. $^{13}$C-pyruvate used in the method of the invention may be isotopically enriched at the C1-position (in the following denoted $^{13}$C$_1$-pyruvate), at the C2-position (in the following denoted $^{13}$C$_2$-pyruvate), at the C3-position (in the following denoted $^{13}$C$_3$-pyruvate), at the C1- and the C2-position (in the following denoted $_{13}$C$_{1,2}$-pyruvate), at the C1- and the C3-position (in the following denoted $^{13}$C$_{1,3}$-pyruvate), at the C2- and the C3-position (in the following denoted $^{13}$C$_{2,3}$-pyruvate) or at the C1-, C2- and C3-position (in the following denoted $^{13}$C$_{1,2,3}$-pyruvate). Isotopic enrichment at the C1-position is preferred since $^{13}$C$_1$-pyruvate has a higher T$_1$ relaxation in human full blood at 37° C. (about 42 s) than $^{13}$C-pyruvate which is isotopically enriched at other C-positions.

Hyperpolarisation of NMR active $^{13}$C-nuclei may be achieved by different methods which are for instance described in described in WO-A-98/30918, WO-A-99/24080 and WO-A-99/35508, which are incorporated herein by reference and hyperpolarisation methods are polarisation transfer from a noble gas, "brute force", spin refrigeration, the parahydrogen method and dynamic nuclear polarisation (DNP).

To obtain hyperpolarised $^{13}$C-pyruvate, it is preferred to either polarise $^{13}$C-pyruvate directly or to polarise $^{13}$C-pyruvic acid and convert the polarised $^{13}$C-pyruvic acid to polarised $^{13}$C-pyruvate, e.g. by neutralisation with a base One suitable way for obtaining hyperpolarised $^{13}$C-pyruvate is the polarisation transfer from a hyperpolarised noble gas which is described in WO-A-98/30918. Noble gases having non-zero nuclear spin can be hyperpolarised by the use of circularly polarised light. A hyperpolarised noble gas, preferably He or Xe, or a mixture of such gases, may be used to effect hyperpolarisation of $^{13}$C-nuclei. The hyperpolarised gas may be in the gas phase, it may be dissolved in a liquid/solvent, or the hyperpolarised gas itself may serve as a solvent. Alternatively, the gas may be condensed onto a cooled solid surface and used in this form, or allowed to sublime. Intimate mixing of the hyperpolarised gas with $^{13}$C-pyruvate or $^{13}$C-pyruvic acid is preferred. Hence, if $^{13}$C-pyruvic acid is polarised, which is a liquid at room temperature, the hyperpolarised gas is preferably dissolved in a liquid/solvent or serves as a solvent. If $^{13}$C pyruvate is polarised, the hyperpolarised gas is preferably dissolved in a liquid/solvent, which also dissolves pyruvate.

Another suitable way for obtaining hyperpolarised $^{13}$C-pyruvate is that polarisation is imparted to $^{13}$C-nuclei by thermodynamic equilibration at a very low temperature and high field. Hyperpolarisation compared to the operating field and temperature of the NMR spectrometer is effected by use of a very high field and very low temperature (brute force). The magnetic field strength used should be as high as possible, suitably higher than 1 T, preferably higher than 5 T, more preferably 15 T or more and especially preferably 20 T or more. The temperature should be very low, e.g. 4.2 K or less, preferably 1.5 K or less, more preferably 1.0 K or less, especially preferably 100 mK or less.

Another suitable way for obtaining hyperpolarised $^{13}$C-pyruvate is the spin refrigeration method. This method covers spin polarisation of a solid compound or system by spin refrigeration polarisation. The system is doped with or intimately mixed with suitable crystalline paramagnetic materials such as Ni$^{2+}$, lanthanide or actinide ions with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The pre-requisite for this method is that the paramagnetic species has a highly anisotropic g-factor. As a result of the sample rotation, the electron paramagnetic resonance will be brought in contact with the nuclear spins, leading to a decrease in the nuclear spin temperature. Sample rotation is carried out until the nuclear spin polarisation has reached a new equilibrium.

In a preferred embodiment, DNP (dynamic nuclear polarisation) is used to obtain hyperpolarised $^{13}$C-pyruvate. In DNP, polarisation of MR active nuclei in a compound to be polarized is affected by a polarisation agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of the DNP agent to the NMR active nuclei of the compound to be polarised, e.g. to the $^{13}$C nuclei in $^{13}$C-pyruvate. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example further described in WO-A-98/58272 and in WO-A-01/96895, both of which are included by reference herein.

To polarise a compound by the DNP method, a mixture of the compound to be polarised and a DNP agent is prepared ("a sample") which is then frozen and inserted into a DNP polariser for polarisation. After the polarisation, the frozen solid hyperpolarized sample is rapidly transferred into the liquid state either by melting it or by dissolving it in a suitable dissolution medium. Dissolution is preferred and the dissolution process of a frozen hyperpolarized sample and suitable devices therefore are described in detail in WO-A-02/37132. The melting process and suitable devices for the melting are for instance described in WO-A-02/36005.

In order to obtain a high polarisation level in the compound to be polarised said compound and the DNP agent need to be in intimate contact during the DNP process. This is not the case if the sample crystallizes upon being frozen or cooled. To avoid crystallization, either glass formers need to be present in the sample or compounds need to be chosen for polarisation which do not crystallize upon being frozen but rather form a glass.

As mentioned earlier $^{13}$C-pyruvic acid or $^{13}$C-pyruvate are suitable starting materials to obtain hyperpolarized $^{13}$C-pyruvate.

Isotopically enriched $^{13}$C-pyruvate is commercially available, e.g. as sodium $^{13}$C-pyruvate. Alternatively, it may be synthesized as described by S. Anker, J. Biol. Chem 176, 1948, 133-1335.

Several methods for the synthesis of $^{13}$C$_1$-pyruvic acid are known in the art. Briefly, Seebach et al., Journal of Organic Chemistry 40(2), 1975, 231-237 describe a synthetic route that relies on the protection and activation of a carbonyl-containing starting material as an S,S-acetal, e.g. 1,3-dithian or 2-methyl-1,3-dithian. The dithiane is metallated and reacted with a methyl-containing compound and/or $^{13}$CO$_2$. By using the appropriate isotopically enriched $^{13}$C-component as outlined in this reference, it is possible to obtain $^{13}$C$_1$-pyruvate, $^{13}$C$_2$-pyruvate or $^{13}$C$_{1,2}$-pyruvate. The carbonyl function is subsequently liberated by use of conventional methods described in the literature. A different synthetic route starts from acetic acid, which is first converted into acetyl bromide and then reacted with Cu$^{13}$CN. The nitrile obtained is converted into pyruvic acid via the amide (see for instance S. H. Anker et al., J. Biol. Chem. 176 (1948), 1333 or J. E. Thirkettle, Chem Commun. (1997), 1025). Further, $^{13}$C-pyruvic acid may be obtained by protonating commercially available sodium $^{13}$C-pyruvate, e.g. by the method described in U.S. Pat. No. 6,232,497 or by the method described in WO-A-2006/038811.

The hyperpolarisation of $^{13}$C-pyruvic acid by DNP is described in detail in WO-A1-2006/011809, which is incorporated herein by reference. Briefly, $^{13}$C-pyruvic acid may be directly used for DNP since it forms a glass when frozen. After DNP, the frozen hyperpolarised $^{13}$C-pyruvic acid needs to be dissolved and neutralised, i.e. converted to $^{13}$C-pyruvate. For the conversion, a strong base is needed. Further, since $^{13}$C-pyruvic acid is a strong acid, a DNP agent needs to be chosen which is stable in this strong acid. A preferred base is sodium hydroxide and conversion of hyperpolarised $^{13}$C-pyruvic acid with sodium hydroxide results in hyperpolarised sodium $^{13}$C-pyruvate, which is the preferred $^{13}$C-pyruvate for an imaging medium which is used for in vivo MR imaging and/or spectroscopy, i.e. MR imaging and/or spectroscopy carried out on living human or non-human animal beings.

Alternatively, $^{13}$C-pyruvate, i.e. a salt of $^{13}$C-pyruvic acid can be used for DNP. Preferred salts are those $^{13}$C-pyruvates which comprise an inorganic cation from the group consisting of $NH_4^+$, $K^+$, $Rb^+$, $Cs^+$, $Ca^{2+}$, $Sr^{2+}$ and $Ba^{2+}$, preferably $NH_4^+$, $K^+$, $Rb^+$ or $Cs^+$, more preferably $K^+$, $Rb^+$, $Cs^+$ and most preferably $Cs^+$, as in detail described in PCT/NO07/00109 and incorporated by reference herein. The synthesis of these preferred $^{13}$C-pyruvates is disclosed in PCT/NO07/00109 as well. If the hyperpolarized $^{13}$C-pyruvate is used in an imaging medium for in vivo MR imaging and/or spectroscopy it is preferred to exchange the inorganic cation from the group consisting of $NH_4^+$, $K^+$, $Rb^+$, $Cs^+$, $Ca^{2+}$, $Sr^{2+}$ and $Ba^{2+}$ by a physiologically very well tolerable cation like $Na^+$ or meglumine. This may be done by methods known in the art like the use of a cation exchange column.

Further preferred salts are $^{13}$C-pyruvates of an organic amine or amino compound, preferably TRIS-$^{13}$C$_1$-pyruvate or meglumine-$^{13}$C$_1$-pyruvate, as in detail described in WO-A2-2007/069909 and incorporated by reference herein. The synthesis of these preferred $^{13}$C-pyruvates is disclosed in WO-A2-2007/069909 as well.

If the hyperpolarised $^{13}$C-pyruvate used in the method of the invention is obtained by DNP, the sample to be polarised comprising $^{13}$C-pyruvic acid or $^{13}$C-pyruvate and a DNP agent may further comprise a paramagnetic metal ion. The presence of paramagnetic metal ions in composition to be polarised by DNP has found to result in increased polarisation levels in the $^{13}$C-pyruvic acid/$^{13}$C-pyruvate as described in detail in WO-A2-2007/064226 which is incorporated herein by reference.

As mentioned earlier, the imaging medium according to the method of the invention may be used as imaging medium for in vivo MR imaging and/or spectroscopy, i.e. MR imaging and/or spectroscopy carried out on living human or non-human animal beings. Such an imaging medium preferably comprises in addition to the MR active agent $^{13}$C-pyruvate an aqueous carrier, preferably a physiologically tolerable and pharmaceutically accepted aqueous carrier like water, a buffer solution or saline. Such an imaging medium may further comprise conventional pharmaceutical or veterinary carriers or excipients, e.g. formulation aids such as are conventional for diagnostic compositions in human or veterinary medicine.

Further, the imaging medium according to the method of the invention may be used as imaging medium for in vitro MR imaging and/or spectroscopy, e.g. for detecting cell death in cell cultures or ex vivo tissues. Such an imaging medium preferably comprises in addition to the MR active agent $^{13}$C-pyruvate a solvent which is compatible with and used for in vitro cell or tissue assays, for instance DMSO or methanol or solvent mixtures comprising an aqueous carrier and a non aqueous solvent, for instance mixtures of DMSO and water or a buffer solution or methanol and water or a buffer solution. As it is apparent for the skilled person, pharmaceutically acceptable carriers, excipients and formulation aids may be present in such an imaging medium but are not required for such a purpose.

In another embodiment, the imaging medium according to the method of the invention comprises non-hyperpolarised lactate, hereinafter denoted lactate.

Suitably, lactate is added in the form of lactic acid or a salt of lactic acid, preferably lithium lactate or sodium lactate, most preferably sodium lactate.

The concentration of hyperpolarised $^{13}$C-pyruvate and lactate in the imaging agent used in the method of the invention is about equal or equal or lactate is present at a lower or higher concentration than $^{13}$C-pyruvate. If for instance the imaging agent contains x M $^{13}$C-pyruvate, it contains x M lactate or about x M lactate or less lactate but preferably not less lactate than a tenth of x M or more lactate but preferably not more lactate than three times x M. In a preferred embodiment, the concentration of lactate in the imaging agent used in the method of the invention is about equal or equal to the concentration of hyperpolarised $^{13}$C-pyruvate. The term "about equal concentration" denotes a lactate concentration which is +/−30% of the concentration of $^{13}$C-pyruvate, preferably +/−20%, more preferably +/−10%.

Lactate is suitably added to the hyperpolarised $^{13}$C-pyruvate after the polarisation process. Several ways of adding the lactate are possible. Where the polarisation process results in a liquid composition comprising the hyperpolarised $^{13}$C-pyruvate, lactate may be dissolved in said liquid composition or a solution of lactate in a suitable solvent, preferably an aqueous carrier may be added to the liquid composition. If the polarisation process results in a solid composition comprising the hyperpolarised $^{13}$C-pyruvate, the lactate may be dissolved in the dissolution medium which is used to dissolve the solid composition. For instance $^{13}$C-pyruvate polarised by the DNP method may be dissolved in an aqueous carrier like water or a buffer solution containing the lactate. If hyperpolarised $^{13}$C-pyruvate has been obtained by DNP, it is preferred to add lactate to the final liquid composition, i.e. to the liquid composition after dissolution/melting of the frozen polarised $^{13}$C-pyruvate/$^{13}$C-pyruvic acid or to the liquid composition after removal of the DNP agent and/or an optional paramagnetic metal ion. Again the lactate may be added as a solid to the liquid composition or dissolved in a suitable solvent, e.g. an aqueous carrier. To promote dissolution of the lactate, several means known in the art, such as stirring, vortexing or sonication may be used. However, methods are preferred which are quid (and do not require a mixing device or help coming into contact with the liquid composition. Methods like vortexing or sonication are thus preferred.

In another embodiment, the imaging medium according to the invention is administered together with lactate. In this embodiment, lactate may be dissolved in a suitable solvent, e.g. an aqueous carrier and administered to a human or non-human animal body or added to a cell culture or ex vivo tissue prior to the administration/addition of the hyperpolarised $^{13}$C-pyruvate ("pre-conditioning") or concomitantly with the administration/addition of the hyperpolarised $^{13}$C-pyruvate.

For pre-conditioning, lactate is preferably administered to a human or non-human animal body 0.5 to 5 minutes prior to the administration of hyperpolarised $^{13}$C-pyruvate and more preferably 1 to 2 minutes prior to the administration of hyperpolarised $^{13}$C-pyruvate. Most preferably, lactate is administered to a human or non-human animal body concomitantly with the administration of hyperpolarised $^{13}$C-pyruvate.

In case of a cell culture or ex vivo tissue, distribution of lactate into the cells occurs faster than in a human or non human animal body since in the latter lactate has to be administered to the vasculature and distribute from the point of administration to the tissue under examination. Hence in case of a cell culture or ex vivo tissue, lactate may be added to said cell culture or ex vivo tissue immediately before hyperpolarised $^{13}$C-pyruvate is added, preferably 2 to 1 minute before hyperpolarised $^{13}$C-pyruvate is added, more preferably 1 to 0.5 minutes and most preferably concomitantly with the addition of hyperpolarised $^{13}$C-pyruvate.

To be used as an imaging medium for in vivo MR imaging or spectroscopy in the method of the invention, the imaging medium comprising the hyperpolarised $^{13}$C-pyruvate and optionally lactate must be suitable for administration to a living human or non-human animal body. The imaging medium preferably comprises an aqueous carrier like water, a buffer or a mixture of buffers as described above. The imaging medium may further comprise conventional pharmaceutically acceptable carriers, excipients and formulation aids. Thus, the imaging medium may for example include stabilizers, osmolality adjusting agents, solubilising agents and the like.

To be used as an imaging medium for in vitro MR imaging or spectroscopy in the method of the invention, the imaging medium comprising the hyperpolarised $^{13}$C-pyruvate and optionally lactate must be suitable to be added to, for instance, cell cultures or ex vivo tissues, and the imaging medium preferably comprises an aqueous carrier like water, a buffer or a mixture of buffers as described above.

If the hyperpolarised $^{13}$C-pyruvate is used as an imaging agent for the detection of cell death in an in vitro method of MR imaging or spectroscopy, e.g. using cell cultures or ex vivo tissue, the imaging medium comprising the hyperpolarised $^{13}$C-pyruvate that is added to the cell culture or ex vivo tissue is 10 mM to 100 mM in $^{13}$C-pyruvate, more preferably 20 mM to 90 mM and most preferably 40 to 80 mM in $^{13}$C-pyruvate.

Cell death can be detected by the method of the invention by following the $^{13}$C-pyruvate signal and the signal of its metabolite $^{13}$C-lactate over time. In viable, e.g. non-apoptotic/non-necrotic cells, the $^{13}$C-pyruvate signal decays over time. The $^{13}$C-lactate signal increases first due to metabolic conversion of $^{13}$C-pyruvate to $^{13}$C-lactate and then slowly decreases mainly due to relaxation. In dying, e.g. apoptotic or necrotic cells, the metabolic conversion of $^{13}$C-pyruvate to $^{13}$C-lactate is greatly decreased and although the $^{13}$C-pyruvate signal decays over time, the $^{13}$C-lactate signal only increases slightly or may not be detectable at all, depending on the degree of cell death/amount of dead cells. Without wanting to be bound to this theory, we believe that this is either due to the loss of activity of the enzyme lactate dehydrogenase which catalyses the interconversion of pyruvate and lactate with concomitant interconversion of NADH and NAD$^+$, and/or due to the loss of the co-factors NADH and NAD$^+$, and/or due to a decrease in cellular lactate concentration.

$^{31}$P-NMR measurements on acid-extracts of EL-4 murine lymphoma cells induced to undergo cell death by treatment with etoposide have demonstrated a decrease in the intensity of the resonances from NAD(H), when compared to untreated control cells. Loss of NAD(H) can be explained by DNA-damage induced activation of the enzyme poly-ADP-ribose polymerase (PARP), which polyadenylates various proteins and uses NAD$^+$ as a substrate. There was also an increase in the resonances from the glycolytic intermediate, fructose-1, 6-bisphosphate (FBP), which can be explained by inhibition of the glycolytic enzyme, glyceraldehyde 3-phosphate dehydrogenase (GAPDH), through loss of its coenzyme NAD(H). Inhibition of PARP activity with a competitive inhibitor (20 mM nicotinamide or 10 mM 3-aminobenzamide) inhibited the loss of NAD(H) and the increase in FBP concentration observed in dying cells.

This loss of NAD(H) due to PARP activation should also inhibit lactate dehydrogenase (LDH) activity and hence the measured flux of $^{13}$C-label between pyruvate and lactate. Consistent with this hypothesis is the observation that cells treated with both nicotinamide and etoposide or nicotinamide and 3-aminobenzamide maintained their ability to transfer the hyperpolarised $^{13}$C-label between the pyruvate and lactate pools, while still exhibiting the common morphological features of dying cells, as detected using fluorescence microscopy.

It has further been found that the addition of lactate—either being present in the imaging medium according to the invention or being added/administered separately—leads to an increased amount of observable $^{13}$C-lactate and thus an increased MR signal from $^{13}$C-lactate.

As explained above, the signal from $^{13}$C-lactate is the signal which is monitored in MR imaging or spectroscopy measurements for detecting cell death and where dying or dead tissue is indicated by a low or absent $^{13}$C-lactate signal, compared to a $^{13}$C-lactate signal one could observe from a viable tissue. An increased signal from $^{13}$C-lactate makes it easier to distinguish between a "low lactate signal" and "no lactate signal" situation, i.e. to distinguish between certain degrees of cell death.

An MR imaging sequence is applied that encodes the volume of interest in a combined frequency and spatially selective way and the $^{13}$C-MR signal of $^{13}$C-pyruvate is followed by MR imaging or spectroscopy over a time period from the addition of the imaging agent (t=0) to about 10 min, preferably 6 min and more preferably 5 min. In the same time period, the appearance, increase and subsequent decrease of the $^{13}$C-lactate signal is monitored. To get a quantitative assessment, MR imaging or spectroscopy of healthy cells or tissue may carried out and the results—i.e. the amount or rate of $^{13}$C-lactate formed over a given time period—may be compared.

If the hyperpolarised $^{13}$C-pyruvate is used as an imaging agent for the detection of cell death in an in vivo method of MR imaging or spectroscopy, e.g. in a living human or non-human animal body, the imaging medium containing the hyperpolarised $^{13}$C-pyruvate is preferably administered to said body parenterally, preferably intravenously. Generally, the body under examination is positioned in the MR magnet. Dedicated $^{13}$C-MR RF-coils are positioned to cover the area of interest. Dosage and concentration of the imaging medium will depend upon a range of factors such as toxicity and the administration route. Generally, the imaging medium is administered in a concentration of up to 1 mmol $^{13}$C-pyruvate per kg bodyweight, preferably 0.01 to 0.5 mmol/kg, more preferably 0.1 to 0.3 mmol/kg. The administration rate is preferably less than 10 ml/s, more preferably less than 6 ml/min and most preferable of from 5 ml/s to 0.1 ml/s. At less than 400 s after the administration, preferably less than 120 s, more preferably less than 60 s after the administration, especially preferably 20 to 50 s an MR imaging sequence is applied that encodes the volume of interest in a combined frequency and spatial selective way. This will result in metabolic images of $^{13}$C-pyruvate and $^{13}$C-lactate. The exact time of applying an MR sequence is highly dependent on the volume of interest for detecting cell death.

The encoding of the volume of interest can be achieved by using so-called spectroscopic imaging sequences as described in for instance T. R. Brown et al., Proc. Natl. Acad. Sci. USA 79, 3523-3526 (1982); A. A. Maudsley, et al., J. Magn. Res 51, 147-152 (1983). Spectroscopic image data contain a number of volume elements in which each element contains a full $^{13}$C-MR spectrum. $^{13}$C-pyruvate and its metabolite $^{13}$C-lactate have their unique position in a $^{13}$C-MR spectrum and their resonance frequency can be used to identify them. The integral of the peak at its resonance frequency is directly related to the amount of $^{13}$C-pyruvate and $^{13}$C-lactate, respectively. When the amount of $^{13}$C-pyruvate and $^{13}$C-lactate is estimated using time domain fitting routines as described for instance in L. Vanhamme et al., J Magn Reson 129, 35-43 (1997), images can be generated for $^{13}$C-pyruvate and $^{13}$C-lactate in which a colour coding or grey coding is representative for the amount of $^{13}$C-pyruvate and $^{13}$C-lactate measured.

Although spectroscopic imaging methods have proven their value in producing metabolic images using all kinds of MR nuclei e.g. $^{1}$H, $^{31}$P, $^{23}$Na the amount of repetitions needed to fully encode the spectroscopic image makes this approach less suitable for hyperpolarised $^{13}$C. Care has to be taken to ensure hyperpolarised $^{13}$C-signal is available during the whole MR data acquisition. At the expense of a reduced signal to noise, this can be achieved by reducing the RF-pulse angle that is applied in every phase encoding step. Higher matrix sizes require more phase encoding steps and longer scan times.

Imaging methods based on the pioneering work of P. C. Lauterbur (Nature, 242, 190-191, (1973) and P. Mansfield (J. Phys. C. 6, L422-L426 (1973)), which apply a readout gradient during the data acquisition, will allow for higher signal to noise images or the equivalent, higher spatial resolution images. However, these imaging methods in their basic form will not be able to produce separate images for $^{13}$C-pyruvate and $^{13}$C-lactate, i.e. the identification of specific metabolites is not possible.

In a preferred embodiment, imaging sequences are used that will make use of multi-echoes to code for the frequency information. Sequences that can produce separate water and fat $^{1}$H-images are for example described in G. Glover, J Magn Reson Imaging 1991; 1:521-530 and S. B. Reeder et al., MRM 51 35-45 (2004). Since the metabolites to be detected and as such their MR frequencies are known, the approach discussed in the references above can be applied to acquire direct images of $^{13}$C-pyruvate and $^{13}$C-lactate. This procedure makes more efficient use of the hyperpolarised $^{13}$C-MR signal, giving a better signal quality compared to spectroscopic imaging, a higher spatial resolution and faster acquisition times.

In a preferred embodiment, the method according to the invention comprises acquiring direct $^{13}$C-MR images or spectra of $^{13}$C-pyruvate and $^{13}$C-lactate from a human or non-human animal body pre-administered with an imaging medium comprising hyperpolarised $^{13}$C-pyruvate or from a cell culture or ex vivo tissue the imaging medium has been added to. In the method described, cell death is identified and detected by a low $^{13}$C-signal intensity from $^{13}$C-lactate or an absent $^{13}$C-signal from $^{13}$C-lactate or a decreased rate of formation of $^{13}$C-lactate.

To correct for the pyruvate signal, both lactate and pyruvate images may be normalized to the maximum value in each individual image. Second, the normalized lactate image is multiplied by the inverted pyruvate image, e.g. the maximum pyruvate signal in the image minus the pyruvate level for every pixel. As a last step, the intermediate result gained in the operation above is multiplied by the original lactate image. Alternatively, the pyruvate and lactate peak intensities in each pixel of their respective images can be fit to a kinetic model of the flux of $^{13}$C-label between pyruvate and lactate to obtain rate constants for label flux and the spin lattice relaxation times. Correction may need to be made for the effect of multiple RF pulses on the loss of polarisation.

Anatomical and/or perfusion information may be included in the detection of cell death according to the method of the invention, if the method is used for detection of cell death in vivo. Anatomical information may for instance be obtained by acquiring a proton or $^{13}$C-MR image with or without employing a suitable contrast agent. Relative perfusion can be determined by using an MR contrast agent like for instance Omniscan™. Likewise, MR imaging techniques for perfusion measurement without the administration of a contrast agent are known in the art. In a preferred embodiment, a non-metabolised hyperpolarised $^{13}C$-contrast agent is used to determine quantitative perfusion. Suitable techniques and contrast agents are for instance described in WO-A-02/23209. In a more preferred embodiment, hyperpolarised $^{13}C$-pyruvate is used to determine quantitative perfusion.

In another preferred embodiment, the imaging medium comprising hyperpolarised $^{13}C$-pyruvate is administered repeatedly, thus allowing dynamic studies. Due to the low toxicity of pyruvate and its favourable safety profile, repeated doses of this compound are well tolerated by the patient.

The results obtained in the method of the invention for instance allow the physician to choose the appropriate treatment for the patient under examination. In a further preferred embodiment, the method of the invention is used to determine whether treatment is successful.

Viewed from a further aspect, the invention provides the use of hyperpolarised $^{13}C$-pyruvate and optionally lactate for the manufacture of an imaging medium for use in a method of $^{13}C$-MR imaging and/or $^{13}C$-MR spectroscopy for detecting cell death. Preferably, the hyperpolarised $^{13}C$-pyruvate used for the manufacture of the imaging medium is obtained by dynamic nuclear polarisation of $^{13}C$-pyruvic acid or $^{13}C$-pyruvate The manufacture and preferred embodiments of the manufacture of hyperpolarised $^{13}C$-pyruvate from $^{13}C$-pyruvic acid or $^{13}C$-pyruvate as well as the manufacture of an imaging medium comprising hyperpolarised $^{13}C$ and optionally lactate is described in detail on page 7 to 11 of this application.

In a preferred embodiment, the invention provides the use of hyperpolarised $^{13}C$-pyruvate and optionally lactate for the manufacture of an imaging medium for use in a method of $^{13}C$-MR imaging and/or $^{13}C$-MR spectroscopy for detecting cell death by acquiring direct $^{13}C$-images and/or $^{13}C$-spectra of $^{13}C$-pyruvate and $^{13}C$-lactate from a human or non-human animal body which has been pre-administered with the imaging medium or from a cell culture or ex vivo tissue to which the imaging medium has been added to.

The aforementioned use and preferred embodiments of this use are described in detail on page 12 to 16 of this application.

BRIEF DESCRIPTION OF THE DRAWINGS

1: $^{13}C_1$-pyruvate intensities (divided by 100) in untreated control cell and etoposide treated cell suspensions
2: $^{13}C_1$-lactate intensities in a control cell suspension
3: $^{13}C_1$-lactate intensities in an etoposide treated cell suspension

Bar numbering in FIG. 2 denote the following:
1: untreated EL4 cell suspension
2: etoposide treated EL4 cell suspension
3: etoposide/nicotinamide treated EL4 cell suspension

EXAMPLES

In the following the terms pyruvate, $^{13}C$-pyruvate and $^{13}C_1$-pyruvate are used interchangeably and all denote $^{13}C_1$-pyruvate. Likewise the terms pyruvic acid, $^{13}C$-pyruvic acid and $^{13}C_1$-pyruvic acid are used interchangeably and all denote $^{13}C_1$-pyruvic acid. Further, the terms lactate, $^{13}C$-lactate and $^{13}C_1$-lactate are used interchangeably and all denote $^{13}C_1$-lactate, unless further specified.

Example 1

Synthesis of Tris(8-carboxy-2,2,6,6-(tetra(methoxyethyl)benzo-[1,2-4,5']bis-(1,3)dithiole-4-yl)methyl sodium salt, a DNP Agent 10 g (70 mmol) Tris(8-carboxy-2,2,6,6-(tetra(hydroxyethyl)benzo-[1,2-4,5']-bis-(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 2

Production of a Composition Comprising Hyperpolarised $^{13}C_1$-Pyruvate Obtained by the DNP Method Using $^{13}C_1$-Pyruvic Acid and the DNP Agent (Trityl Radical) of Example 1

A 20 mM solution was prepared by dissolving 5.0 mg of the radical of Example 1 in $^{13}C_1$-pyruvic acid (164 μl). The sample was mixed to homogeneity and an aliquot of the solution (41 mg) was placed in a sample cup and inserted in the DNP polariser.

The sample was polarised under DNP conditions at 1.2 K in a 3.35 T magnetic field under irradiation with microwave (93.950 GHz). After 2 hours the polarisation was stopped and the sample was dissolved using a dissolution device according to WO-A-02/37132 in an aqueous solution of sodium hydroxide and tris(hydroxymethyl)-aminomethane (TRIS) to provide a neutral solution of hyperpolarised sodium $^{13}C_1$-pyruvate. The dissolved sample was rapidly analysed with $^{13}C$-NMR to assess the polarisation and a 19.0% $^{13}C$-polarisation was obtained.

Example 3

Production of a Composition Comprising Hyperpolarised $^{13}C_1$-Pyruvate Obtained by the DNP Method Using $^{13}C$-Pyruvic Acid and the DNP Agent (Trityl Radical) of Example 1

A 15 mM solution was prepared by dissolving the radical of Example 1 (209.1 mg) in a mixture of $^{13}C_1$-pyruvic acid (553 mg) and unlabelled pyruvic acid (10.505 g). The sample was mixed to homogeneity and an aliquot of the solution (2.015 g) was placed in a sample cup and inserted in the DNP polariser.

The sample was polarised under DNP conditions at 1.2 K in a 3.35 T magnetic field under irradiation with microwave (93.950 GHz). After 4 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarised sodium $^{13}C_1$-pyruvate with a total pyruvate concentration of 0.5 M in 100 mM TRIS buffer. In series with the dissolution device a chromatographic column was connected. The column consists of a cartridge (D=38 mm; h=10 mm) containing hydrophobic packing material (Bondesil-C18, 40UM Part #:12213012) supplied by Varian. The dissolved sample was forced through the column which selectively adsorbed the radical. The filtered solution was rapidly analysed with $^{13}C$-NMR to assess the polarisation, 16.5% $^{13}C$ polarisation was obtained. The residual radical concentration was subsequently analysed with a UV spectrophotometer meter at 469 nm and was determined to be below the detection limit of 0.1 µM.

Example 4

Production of Hyperpolarised $^{13}C_1$-Pyruvate by the DNP Method using $^{13}C_1$-pyruvic acid and Tris(8-carboxy-2,2,6,6-tetra(hydroxy-ethoxy)methyl-benzo[1,2-d:4,5-d']bis(1,3)dithiole-4-yl)methyl Sodium Salt as DNP Agent Tris(8-carboxy-2,2,6,6-tetra(hydroxyethoxy)methyl-benzo[1,2-d:4,5-d']-bis-(1,3)-dithiole-4-yl)methyl sodium salt was synthesised as described in Example 29 in WO-A-97/09633.

A 20 mM solution was prepared by dissolving Tris(8-carboxy-2,2,6,6-tetra(hydroxyethoxy)methyl-benzo[1,2-d:4,5-d']-bis-(1,3)-dithiole-4-yl)methyl sodium salt in $^{13}C_1$-pyruvic acid (83.1 mg). The sample was mixed to homogeneity, placed in a sample cup and inserted in the DNP polariser. The sample was polarised under DNP conditions at 1.2 K in a 3.35 T magnetic field under irradiation with microwave (93.950 GHz). The $^{13}C$-NMR signal from the sample was acquired using a Varian Inova-200 NMR spectrometer.

The DNP enhancement was calculated from a measurement of the thermal equilibrium $^{13}C$-NMR signal and the enhanced NMR signal. 16% $^{13}C$— polarisation was obtained.

Example 5

Preparation of an Imaging Medium Comprising Hyperpolarised $^{13}C_1$-Pyruvate and Non-Hyperpolarised Non-Labelled Lactate A 15 mM solution was prepared by dissolving the DNP agent (trityl radical) of Example 1 in $^{13}C_1$-pyruvic acid (44 mg, 91%). The sample was mixed to homogeneity and the solution was placed in a sample cup and inserted in the DNP polariser.

The sample was polarised under DNP conditions at 1.2 K in a 3.35 T magnetic field under irradiation with microwave (94 GHz and 100 mW, respectively). Polarisation was followed by solid state NMR. After 90 min hyperpolarisation, the sample was dissolved in 6 ml of an aqueous solution of 94 mM NaOH, 30 mM NaCl, 40 mM HEPES and 50 mg/liter EDTA. The pH of the dissolved sample was 7.4 with a final $^{13}C_1$-pyruvate concentration of 75 mM.

2 ml of the solution were combined with a solution of 500 µl water containing 18 mg lithium lactate to result in an imaging medium comprising 60 mM hyperpolarised $^{13}C_1$-pyruvate and 75 mM lactate.

Example 6

Detection of Cell Death in Cell Cultures 6.1 Preparation of EL4 Cells

EL4 murine lymphoma cells ($10^8$ cells) were treated with 15 µM etoposide (PCH Pharmachemie BV, Harleem), a compound which is known to induce cell death after 16 h exposure. A separate set of cells was treated for 16 hours with 15 µM etoposide plus 20 mM nicotinamide, a known PARP inhibitor. Cell death (apoptosis and necrosis) was confirmed by acridine orange and propidium iodide staining. The cells were washed 3 times with RPMI 1640 growth medium containing 10% FCS at 37° C. and to 2 ml of the etoposide- and etoposide/nicotinamide treated EL4 cell suspension 2 ml of the imaging medium according to Example 5 were added. The final cell suspension thus contained 30 mM hyperpolarised $^{13}C_1$-pyruvate and 37.5 mM lactate.

Figure 1:
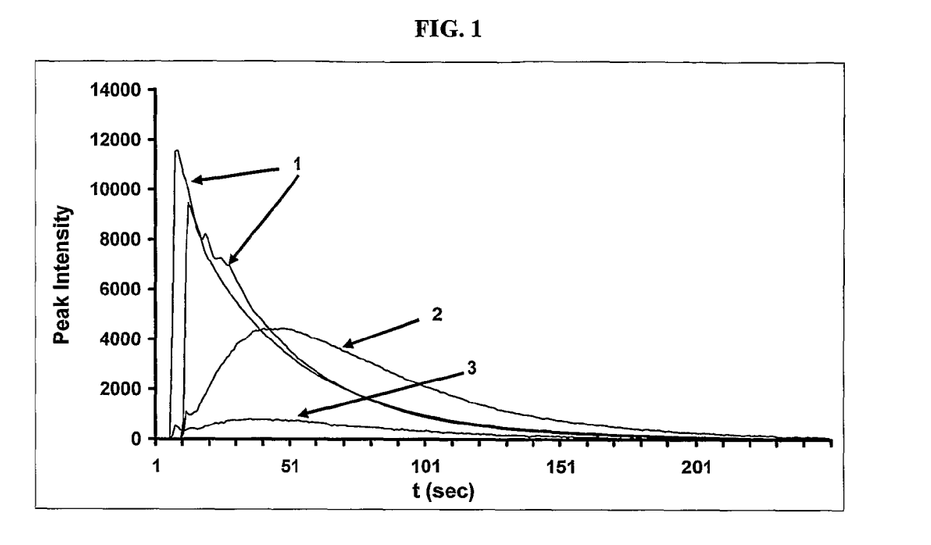
FIG. 1 depicts peak intensities of $^{13}C_1$-pyruvate and $^{13}C_1$-lactate in an EL4 cell suspension treated with etoposide and in an untreated EL4 cell suspension vs. time. Curve numberings in FIG. 1 denote the following.

6.2 $^{13}C$-MR Spectroscopy of EL4 Cells $^{13}C$-signal intensities from $^{13}C$-pyruvate and $^{13}C$-lactate in etoposide-treated EL4 cell suspensions as described in 6.1 were followed over a time period of 240 seconds from the time of addition of the imaging medium. One $^{13}C$. spectrum per second was acquired using low flip angle pulses at 9.4 T for a total of 240 spectra. A control of non-etoposide treated (untreated) EL4 lymphoma cells was also examined, as outlined above, and the peak intensities of $^{13}C$-pyruvate and $^{13}C$-lactate from the untreated and the etoposide were plotted on a graph (FIG. 1).

Figure 2:
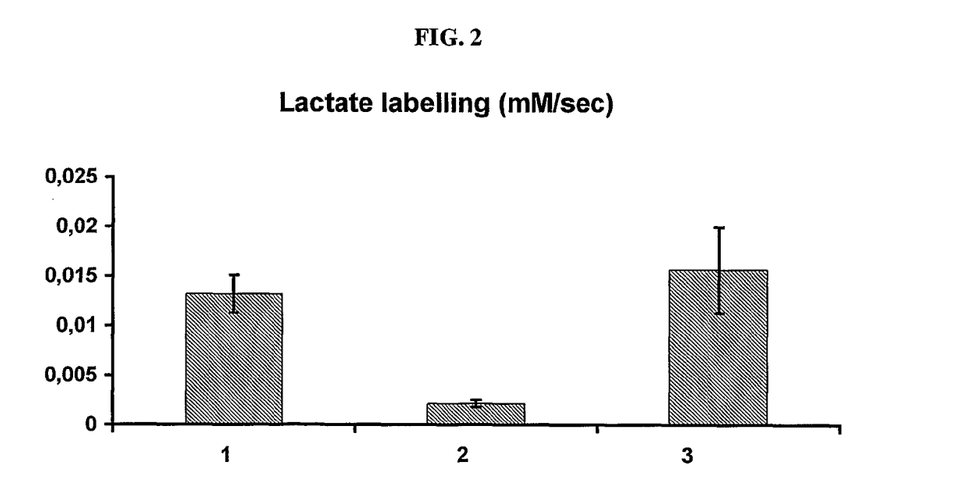
FIG. 2 shows the effect of etoposide and etoposide/nicotinamide treatment on EL4 cells to the cell death inducing drug etoposide. Bar graphs in FIG. 2 represent 3 experiments+/− standard deviation.

6.3 $^{13}C$-MR Spectroscopy of EL4 Cells $^{13}C$-signal intensities from $^{13}C$-pyruvate and $^{13}C$-lactate in etoposide-treated and etoposide/nicotinamide treated EL4 cell suspensions as described in 6.1 were followed over a time period of 240 seconds from the time of addition of the imaging medium. One $^{13}C$ spectrum per second was acquired using low flip angle pulses at 9.4 T for a total of 240 spectra. A control of non-etoposide treated (untreated) EL4 lymphoma cells was also examined, as outlined above, and the peak intensities of $^{13}$C-pyruvate and $^{13}$C-lactate from the untreated, the etoposide treated and the etoposide/nicotinamide treated EL4 cells were compared. The data were fit to a two-site exchange model based on the modified Bloch equations, and the rate constants for the forward and reverse exchange $^{13}$C-fluxes were determined. Bar graphs in FIG. 2 represent 3 experiments+/−standard deviation.

Example 7

Preparation of an Imaging Medium Comprising Hyperpolarised $^{13}$C$_1$-Pyruvate A 15 mM solution was prepared by dissolving the DNP agent (trityl radical) of Example 1 in $^{13}$C$_1$-pyruvic acid (44 mg, 91%). The sample was mixed to homogeneity and the solution was placed in a sample cup and inserted in the DNP polariser.

The sample was polarised under DNP conditions at 1.2 K in a 3.35 T magnetic field under irradiation with microwave (94 GHz and 100 mW, respectively). Polarisation was followed by solid state NMR. After 90 min hyperpolarisation, the sample was dissolved in 6 ml of an aqueous solution of 94 mM NaOH, 30 mM NaCl, 40 mM HEPES and 50 mg/liter EDTA. The pH of the dissolved sample was 7.4 with a final $^{13}$C$_1$-pyruvate concentration of 75 mM.

Example 8

Detection of Cell Death In Vivo

Lymphoma tumours were produced in mice by subcutaneous implantation of EL4 cells. The mice were treated with an i.p. injection of 67 mg/kg etoposide. Tumour cell death following etoposide treatment was assessed histologically. Non-etoposide treated mice were used as control.

Figure 3A:
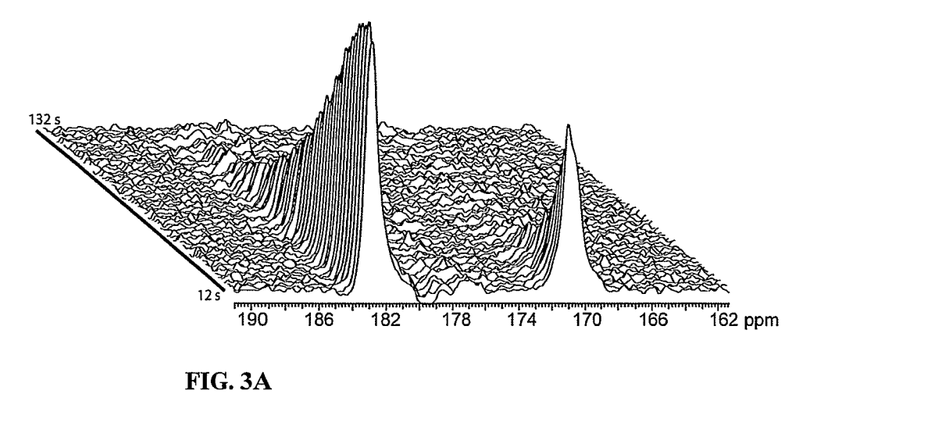
FIG. 3A shows a representative series of $^{13}C$ MR spectra from a 5 mm thick slice through a tumour prior etoposide treatment following the i.v. injection of 0.2 ml of 75 mM hyperpolarised $^{13}C_1$-pyruvate. The resonance at 171 ppm is from $^{13}C_1$-pyruvate, the resonance at 183 ppm is from $^{13}C_1$-lactate.
Figure 3B:
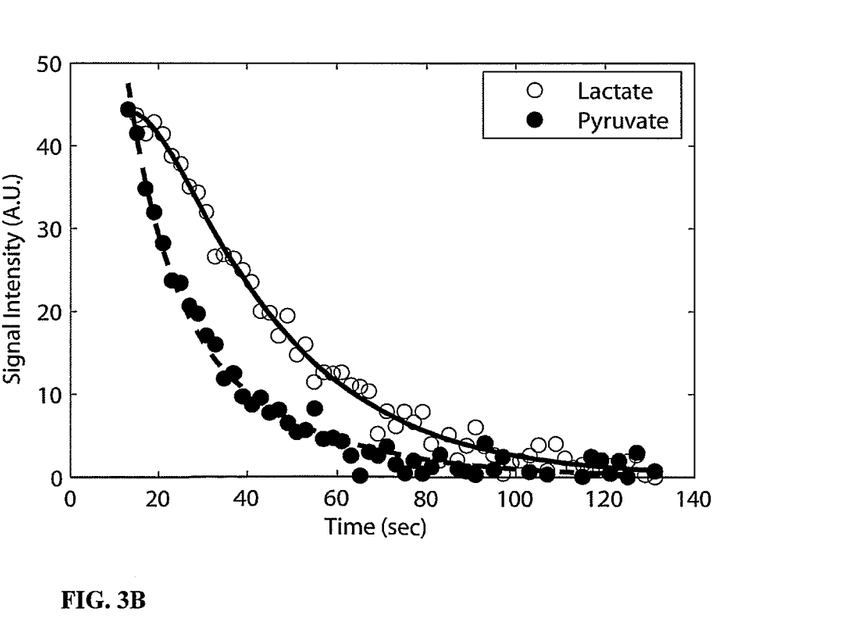
FIG. 3B shows tumour $^{13}C_1$-pyruvate (closed symbols) and $^{13}C_1$-lactate (open symbols) peak intensities following the i.v. injection of 0.2 ml of 75 mM hyperpolarised $^{13}C_1$-pyruvate. The solid lines show the fit to the two-site exchange model.

Intravenous injection of hyperpolarized $^{13}$C$_1$-pyruvate of Example 7 (0.2 ml) resulted in readily measurable signals from $^{13}$C-pyruvate and lactate in the tumour (FIG. 3A) Spectra were collected every 2 s for two min starting from 12 s after the beginning of the injection. Measurements from an imaging slice in underlying muscle and from a slice above the tumour, which passed through the liver, showed signal from pyruvate but only small signals from lactate in etoposide-treated and untreated animals. The time-dependent changes in the tumour signals from lactate and pyruvate were fit to the exchange model to obtain the apparent rate constants, and spin lattice relaxation times (FIG. 3B). The first 10-15 s of data acquisition were lost since this was the time taken to complete the injection and insert the $^{13}$C surface coil probe assembly, containing the animal, into the imaging magnet.

Figure 3C:
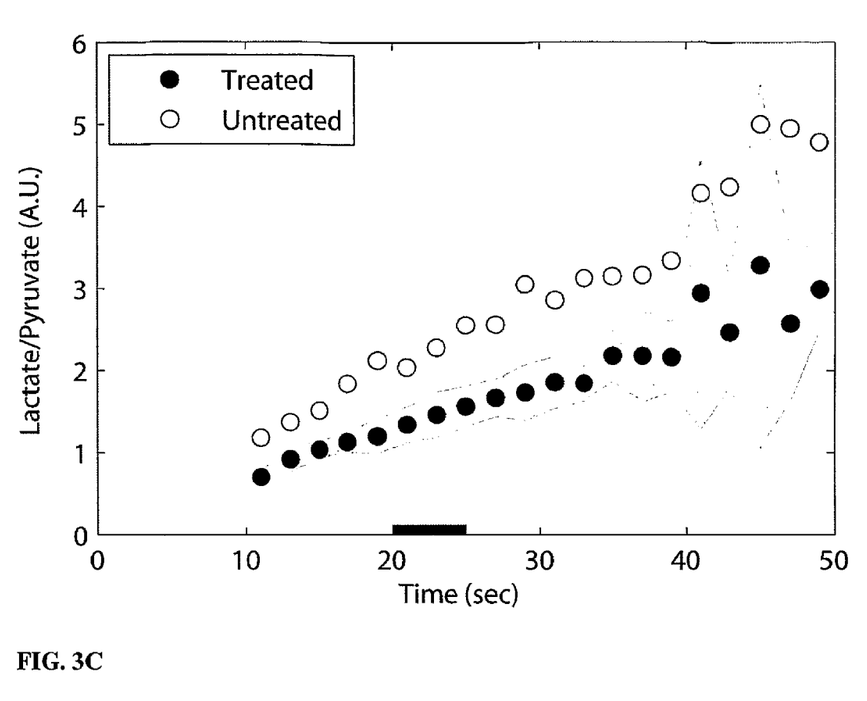
FIG. 3C shows the $^{13}C_1$-lactate/$^{13}C_1$-pyruvate peak intensity ratio following the i.v. injection of 0.2 ml of 75 mM hyperpolarised $^{13}C_1$-pyruvate in mice with untreated (open symbols) and etoposide-treated (closed symbols) tumours. The shaded regions represent one SD from the mean (n=8 for both animal groups). The black bar between 20 and 25 s indicates the time period when $^{13}C$-spectroscopic MR imaging was performed.

Treatment of EL-4 tumour-bearing animals with etoposide, resulted in 37.0±3.8% cell death 24 h after drug treatment, as compared to 4.8±0.7% in the control group (n=3, P<0.01), and there was a small decrease in tumour volume, from 1.6±0.4 cm$^3$ (n=8) in untreated tumours to 1.3±0.2 cm$^3$ (n=8) in treated tumours (determined from multi-slice $^1$H spin echo images). Etoposide treatment resulted in an approximately 25% decrease in the rate constant $k_P^{app}$, measured following injection of hyperpolarized $^{13}$C-pyruvate. The rate constant was 0.075±0.011 s$^{-1}$ in control tumours and 0.056±0.005 s$^{-1}$ in etoposide-treated tumours (n=8, p<0.01). The difference in rate constants cannot be explained by differences in pyruvate delivery to the tumours, since the pyruvate concentrations determined by $^1$H NMR measurements on perchloric acid-extracts of freeze-clamped tumours were 0.55±0.19 µmmol/g wet wt. (n=8) in control tumours and 0.75±0.48 µmol/g wet wt. (n=8) in etoposide-treated tumours. The decreased $^{13}$C-label flux between pyruvate and lactate was readily observable from a plot of the labelled lactate/pyruvate ratios (FIG. 3C), which showed a nearly complete separation of the two groups of animals. The data were collected 20 h after treatment of the animals with etoposide. The increased SDs after 40 s reflect the decrease in signal-to-noise on the lactate and pyruvate resonances resulting from the loss of polarisation. The calculated equilibrium lactate/pyruvate ratios (i.e. $L_\infty/P_\infty$, equivalent to the concentration ratio) showed a decrease from 4.0±0.8 (n=8) in control tumours to 2.7±0.4 (n=8) (p<0.005) in etoposide-treated tumours. A similar decrease was observed in the lactate/pyruvate ratio measured by $^1$H NMR measurements on perchloric acid extracts of freeze-clamped tumours, where the ratio decreased from 9.5±3.5 (n=8) to 5.1±2.0 (n=8) (p<0.01). These extracts were made immediately following completion of the MR experiments. The lactate concentrations in etoposide-treated and untreated tumours in animals that had not been injected with pyruvate were 3.6±0.2 µmol/g wet wt. and 3.0±0.6 µmol/g wet wt. (n=3) respectively. These values were not statistically significantly different from the corresponding values in pyruvate-injected animals, which were 3.2±1.3 µmol/g wet wt. and 5.0±1.9 µmol/g wet wt. respectively (n=8). Enzyme activity measurements on protein extracts prepared from freeze-clamped tumours showed a decrease in LDH concentration from 350±200 units/g wet wt. in untreated tumours (n=5) to 100±20 units/g wet wt. in drug-treated tumours (n=3) (p<0.05).

In another series of experiments, animals were etoposide-treated 24 h after imaging and then 24 h after etoposide treatment a second set of images were acquired, thus each animal could serve as its own control. However, as with the other experiments, there was little variation within the groups and the group results are presented. The rate constant was 0.065±0.017 s$^{-1}$ before treatment and 0.040+0.012 s$^{-1}$ following treatment (n=4, p<0.01), representing a 39% decrease in flux.

The invention claimed is:

1. A method of $^{13}$C-MR imaging and/or $^{13}$C-MR spectroscopy for detecting cell death comprising
   (a) administration of an imaging medium comprising hyperpolarised $^{13}$C-pyruvate to a human body, a non-human animal body, a cell culture, or ex-vivo tissue;
   (b) administration of non-hyperpolarised lactate to said human body, a non-human animal body, a cell culture, or ex-vivo tissue prior to the administration of said imaging medium; and
   (c) subjecting said human body, a non-human animal body, a cell culture, or ex-vivo tissue to $^{13}$C-MR imaging or $^{13}$C-MR spectroscopy following administration of the hyperpolarized $^{13}$C-pyruvate.

2. The method as claimed in claim 1 wherein the imaging medium and lactate are administered to a human or non-human animal body and said $^{13}$C-MR imaging and/or $^{13}$C-MR spectroscopy is carried out for detecting cell death in said human or non-human animal body.

3. The method as claimed in claim 1 wherein the imaging medium is added to a cell culture or ex vivo tissue and said $^{13}$C-MR imaging and/or $^{13}$C-MR spectroscopy is carried out for detecting cell death in said cell culture or ex vivo tissue.

4. The method as claimed in claim 1 wherein $^{13}$C-signal intensities from the $^{13}$C-pyruvate and its metabolite $^{13}$C-lactate are followed by $^{13}$C-MR imaging or $^{13}$C-MR spectroscopy over time.

5. The method as claimed in claim 4 wherein the $^{13}$C-signal intensities from $^{13}$C-pyruvate and $^{13}$C-lactate are followed by $^{13}$C-MR imaging or $^{13}$C-MR spectroscopy from the time point of the administration of the imaging medium to about 10 min.

6. The method as claimed in claim 1 wherein cell death is detected by a low $^{13}$C-signal intensity from $^{13}$C-lactate or absent $^{13}$C-signal from $^{13}$C-lactate or a lowered rate of formation of $^{13}$C-lactate.

7. The method as claimed in claim 1 wherein the hyperpolarised $^{13}$C-pyruvate is obtained by dynamic nuclear polarisation of $^{13}$C-pyruvic acid or $^{13}$C-pyruvate.

8. The method as claimed in claim 5 wherein the $^{13}$C-signal intensities from $^{13}$C-pyruvate and $^{13}$C-lactate are followed by $^{13}$C-MR imaging or $^{13}$C-MR spectroscopy from the time point of the administration of the imaging medium to about 6 min.

9. The method as claimed in claim 5 wherein the $^{13}$C-signal intensities from $^{13}$C-pyruvate and $^{13}$C-lactate are followed by $^{13}$C-MR imaging or $^{13}$C-MR spectroscopy from the time point of the administration of the imaging medium to about 5 min.

* * * * *